US012616892B2

(12) United States Patent
    Kobayashi

(10) Patent No.:    US 12,616,892 B2
(45) Date of Patent:        May 5, 2026

(54) INFORMATION PROCESSING DEVICE, INFORMATION PROCESSING METHOD, AND NON-TRANSITORY COMPUTER-READABLE STORAGE MEDIUM STORING PROGRAM

(71) Applicant: SEIKO EPSON CORPORATION, Tokyo (JP)

(72) Inventor: Shinichi Kobayashi, Azumino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 369 days.

(21) Appl. No.: 18/235,176

(22) Filed: Aug. 17, 2023

(65) Prior Publication Data

US 2024/0058685 A1      Feb. 22, 2024

(30) Foreign Application Priority Data

Aug. 18, 2022    (JP) ................................. 2022-130584

(51) Int. Cl.
    *A63B 71/06*        (2006.01)
    *A61B 5/00*         (2006.01)
    *A63B 24/00*        (2006.01)

(52) U.S. Cl.
    CPC ........ *A63B 71/0622* (2013.01); *A61B 5/7235* (2013.01); *A63B 24/0006* (2013.01); *A63B 24/0075* (2013.01)

(58) Field of Classification Search
    CPC ............ A63B 71/0622; A63B 24/0006; A63B 24/0075; A61B 5/7235
    See application file for complete search history.

(56) References Cited

U.S. PATENT DOCUMENTS

| | | | | |
|---|---|---|---|---|
| 10,058,756 | B1 * | 8/2018 | Basilone | A63B 69/0002 |
| 10,894,198 | B1 * | 1/2021 | Teeger | A63B 71/0605 |
| 11,117,035 | B2 * | 9/2021 | Stemle | A63B 69/0002 |
| 11,458,362 | B1 * | 10/2022 | Berme | G09B 19/0038 |
| 11,679,299 | B2 * | 6/2023 | Power | A63B 24/0062 |
| | | | | 482/8 |
| 11,790,536 | B1 * | 10/2023 | Berme | G06T 7/70 |
| | | | | 382/107 |
| 2003/0134724 | A1 * | 7/2003 | Tuttle | A63B 21/4001 |
| | | | | 482/105 |
| 2009/0170642 | A1 * | 7/2009 | Ono | A63B 24/0021 |
| | | | | 473/455 |

(Continued)

FOREIGN PATENT DOCUMENTS

| | | |
|---|---|---|
| JP | 2020034849 A | 3/2020 |
| JP | 2022-061784 A | 4/2022 |

*Primary Examiner* — Malina D. Blaise
(74) *Attorney, Agent, or Firm* — OLIFF PLC.

(57) ABSTRACT

An information processing device includes a control unit, provided that information indicating evaluation about a first exercise is evaluation information, inputting input information including the evaluation information about a first person and respective pieces of the evaluation information about a plurality of model persons to a trained machine learning model being configured to, when the input information is input, output model person information indicating a model person appropriate for a goal of the first person among the plurality of model persons, and outputting output information including the model person information output from the machine learning model.

11 Claims, 6 Drawing Sheets

(56)     References Cited

U.S. PATENT DOCUMENTS

| | | | |
|---|---|---|---|
| 2011/0003653 A1* | 1/2011 | Stemle | A63B 63/007 |
| | | | 473/456 |
| 2016/0279496 A1* | 9/2016 | Lee | G06Q 10/0639 |
| 2016/0307335 A1* | 10/2016 | Perry | G06T 7/292 |
| 2017/0100658 A1* | 4/2017 | Tally | A63B 69/0002 |
| 2017/0151481 A1* | 6/2017 | Divine | A63B 71/10 |
| 2017/0200277 A1* | 7/2017 | Keat | G06T 7/248 |
| 2017/0333777 A1* | 11/2017 | Spivak | G06V 20/42 |
| 2017/0361188 A1* | 12/2017 | Jang | A63B 69/0002 |
| 2018/0001179 A1* | 1/2018 | Larson | A63B 63/008 |
| 2018/0052228 A1* | 2/2018 | Markison | A63B 71/06 |
| 2018/0207508 A1* | 7/2018 | Lee | A63B 69/0002 |
| 2018/0272224 A1* | 9/2018 | Chen | G06V 40/28 |
| 2020/0074380 A1 | 3/2020 | Mori et al. | |
| 2020/0394413 A1* | 12/2020 | Bhanu | G06N 3/045 |
| 2021/0315468 A1* | 10/2021 | Fujimoto | A61B 5/02055 |
| 2021/0319618 A1* | 10/2021 | Lee | H04N 13/117 |
| 2023/0034143 A1* | 2/2023 | Thatha | A63B 71/0622 |
| 2023/0355186 A1* | 11/2023 | Tanaka | A61B 5/7275 |
| 2023/0372803 A1* | 11/2023 | Kweon | A63B 71/0669 |
| 2023/0405402 A1* | 12/2023 | Zucchetto | A63B 71/0622 |
| 2024/0009515 A1* | 1/2024 | Hörnsten Nilsson | |
| | | | A63B 24/0006 |
| 2024/0173608 A1* | 5/2024 | Schembs | A63B 71/06 |

* cited by examiner

INFORMATION PROCESSING DEVICE, INFORMATION PROCESSING METHOD, AND NON-TRANSITORY COMPUTER-READABLE STORAGE MEDIUM STORING PROGRAM

The present application is based on, and claims priority from JP Application Serial Number 2022-130584, filed Aug. 18, 2022, the disclosure of which is hereby incorporated by reference herein in its entirety.

BACKGROUND

1. Technical Field

This disclosure relates to an information processing device, an information processing method, and a non-transitory computer-readable storage medium storing a program.

2. Related Art

Technologies for supporting people to perform exercises have been researched and developed.

In this regard, a known information processing device acquires data about an exercise of a user, calculates a difference between the acquired data and data about an exercise of a possible model person of the user, and outputs information indicating advice for compensating for the calculated difference (see JP-A-2022-061784).

However, the information processing device described in JP-A-2022-061784 cannot output a desired person of the user as the possible model person of the user. Thus, the information processing device may cause the user to aspire to be a person different from a person whom the user should aspire to be.

SUMMARY

According to an aspect of the present disclosure for solving the above problem, an information processing device includes a control unit configured to use information indicating evaluation about a first exercise as evaluation information, input input information including the evaluation information about a first person and respective pieces of the evaluation information about a plurality of model persons to a machine learning model trained, and output output information including model person information indicating a model person, among the plurality of model persons, corresponding to similar evaluation information output from the machine learning model, the machine learning model being configured to, when the input information is input, output, as the similar evaluation information, a piece of the evaluation information that, among respective pieces of the evaluation information of the plurality of model persons, is estimated to be most easily approachable by the evaluation information about the first person.

According to another aspect of the present disclosure, an information processing method includes, provided that information indicating evaluation about a first exercise is evaluation information, inputting input information including the evaluation information about a first person and respective pieces of the evaluation information about a plurality of model persons to a machine learning model trained, and outputting output information including model person information indicating a model person, among the plurality of model persons, corresponding to similar evaluation information output from the machine learning model, the machine learning model being configured to, when the input information is input, output, as the similar evaluation information, a piece of the evaluation information that, among respective pieces of the evaluation information of the plurality of model persons, is estimated to be most easily approachable by the evaluation information about the first person.

According to still another aspect of the present disclosure, a non-transitory computer-readable storage medium stores a program, the program causing a computer to execute, provided that information indicating evaluation about a first exercise is evaluation information, inputting input information including the evaluation information about a first person and respective pieces of the evaluation information about a plurality of model persons to a machine learning model trained, and outputting output information including model person information indicating a model person, among the plurality of model persons, corresponding to similar evaluation information output from the machine learning model, the machine learning model being configured to, when the input information is input, output, as the similar evaluation information, a piece of the evaluation information that, among respective pieces of the evaluation information of the plurality of model persons, is estimated to be most easily approachable by the evaluation information about the first person.

DESCRIPTION OF EMBODIMENTS

Embodiment

Figure 1:
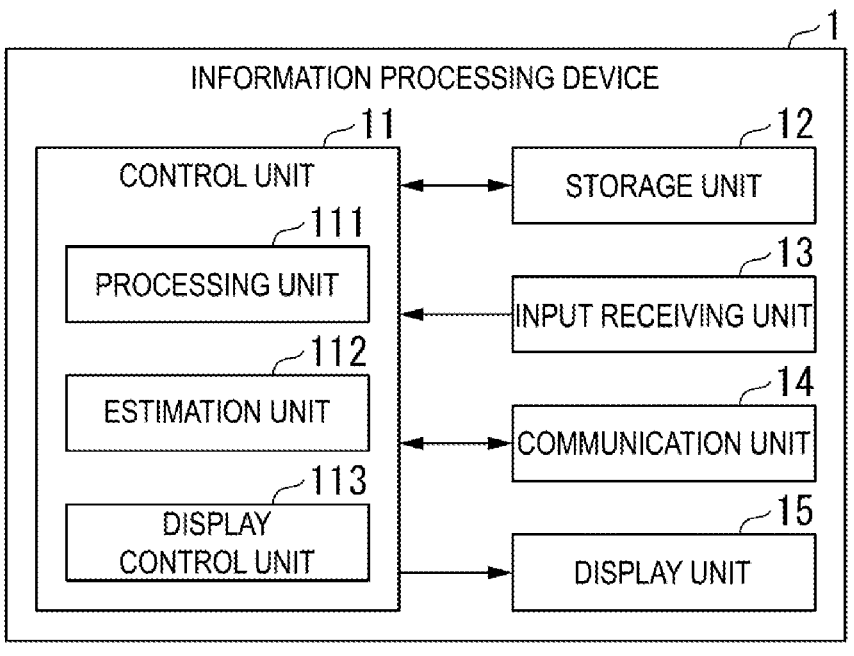
FIG. 1 is a diagram illustrating an example of a configuration of an information processing device 1.

An embodiment of the present disclosure will be described below with reference to the drawings.

Overview of Information Processing Device

First, an overview of an information processing device according to the embodiment will be described.

The information processing device according to the embodiment uses information indicating evaluation about a first exercise as evaluation information. Moreover, the information processing device includes a control unit. The control unit performs processing using a trained machine learning model. When input information including evaluation information about a first person and evaluation information about each of a plurality of model persons is input, the machine learning model outputs, as similar evaluation information, evaluation information that, among respective pieces of the evaluation information of the plurality of model persons, is estimated to be most easily approachable by the evaluation information about the first person. Thus, as this processing, the control unit performs processing of inputting the input information to the trained machine learning model and outputting output information including model person information indicating a model person, among the plurality of model persons, corresponding to the similar evaluation information output from the machine learning model. Accordingly, the information processing device can accurately output the model person information indicating the model person appropriate as a goal of the user.

A configuration of the information processing device according to the embodiment and processing performed by the information processing device will be described below in detail.

Configuration of Information Processing Device

The configuration of the information processing device according to the embodiment will be described below with an information processing device 1 as an example. For convenience of description, a user of the information processing device 1 will be simply referred to as a user below. In addition, for convenience of description, an exercise performed by the user will be referred to as a first exercise below. Examples of the first exercise include baseball, soccer, volleyball, and marathon, but the first exercise is not limited thereto. As an example, a case in which the first exercise is baseball will be described below. Moreover, in the following description, information indicating evaluation about the first exercise will be referred to as evaluation information for convenience of description. Furthermore, in the following description, each of a plurality of persons cited as a person who is a goal for a person who performs the first exercise such as the user will be referred to as a model person for convenience of description. Examples of the model person include a player in a professional league of the first exercise and a player who has achieved excellent results in various competitions of the first exercise, but the model person is not limited thereto. Moreover, in the following description, each of a plurality of types representing how to use the body in the first exercise will be referred to as a physical type for convenience of description. When the first exercise is baseball as in this example, examples of the plurality of physical types include a contact type, a power type, a speed type, a defense type, and a balance type. Here, the contact type is a physical type representing a way of using the body specialized in a technique of contacting a ball thrown by a pitcher with a bat. The power type is a physical type representing a way of using the body specialized in a technique of flying the ball thrown by the pitcher far away using muscle force. The speed type is a physical type representing a way of using the body specialized in a technique of running fast. The defense type is a physical type representing a way of using the body specialized in a technique of defense. The balance type is a physical type representing a way of using the body to perform all techniques of baseball on average. In addition, for convenience of description, a case will be described below in which attribute information indicating an attribute of a certain person includes age group information indicating an age group of the person and physique information indicating a physique of the person. Further, the attribute information may include the age group information or the physique information. In addition to the age group information and the physique information or instead of at least one of the age group information or the physique information, the attribute information may include information indicating another attribute of the person such as a flag indicating whether the person is a professional league player. When the first exercise is baseball as in this example, the professional league is a professional baseball league. Moreover, as an example, a case will be described below in which the age group of a certain person is classified into an elementary school student, a junior high school student, a high school student, a college student, a working adult, and the like. Further, the age group of the person may be classified by another method such as a method using age. Furthermore, as an example, a case will be described below in which the physique of a certain person is represented by a combination of the height and the weight of the person. Further, in addition to the height and the weight of the person or instead of at least one of the height or the weight of the person, the physique of the person may be represented by another value indicating the physique of the person.

FIG. 1 is a diagram illustrating an example of the configuration of the information processing device 1.

The information processing device 1 provides the user with a model person appropriate as a goal of the user among a plurality of model persons. More specifically, the information processing device 1 provides the user with the model person through the following processing.

For example, the information processing device 1 displays a graphical user interface (GUI) for receiving user attribute information indicating an attribute of the user and receives the user attribute information via the displayed GUI. Here, model person information indicating each of the plurality of model persons is stored in the information processing device 1. Examples of the model person information indicating a certain model person include model person identification information for identifying the model person, physical type information indicating a physical type of the model person, and model person attribute information indicating an attribute of the model person. The model person identification information is, for example, an identifier (ID) for identifying the model person, but may be other information capable of identifying the model person. Further, the model person information may include other information indicating the model person in addition to these three pieces of information or instead of at least one of these three pieces of information.

After receiving the user attribute information, the information processing device 1 identifies, based on the received user attribute information, model person information indicating each of one or more model persons estimated to be a goal of the user in the first exercise from among the plurality of pieces of model person information stored in advance. Specifically, the information processing device 1 identifies, from among the plurality of pieces of model person information stored in advance, one or more pieces of model person information including model person attribute information indicating an attribute matching the attribute indicated by the received user attribute information as model person information indicating each of the one or more model persons estimated to be a goal of the user in the first exercise. Further, the information processing device 1 may be configured to identify the one or more pieces of model person information by another method.

After identifying the one or more pieces of model person information, the information processing device 1 estimates, as similar evaluation information, evaluation information to which the evaluation information about the user is estimated to become close most easily among respective pieces of the evaluation information of the plurality of model persons, based on the evaluation information about the model person indicated by each of the identified one or more pieces of model person information and the evaluation information about the user. Here, the evaluation information about each of the plurality of model persons is stored in advance in the information processing device 1. The evaluation information about a certain model person is associated with the model person identification information for identifying the model person. Thus, the information processing device 1 can identify the evaluation information about the model person indicated by each of the identified one or more pieces of model person information. In addition, the information processing device 1 may be configured to store the evaluation information about the user in advance or may be configured to generate the evaluation information about the user. As an example, a case will be described below in which the evaluation information about the user is stored in advance in the information processing device 1. Details of the evaluation information will be described below.

The information processing device 1 estimates the similar evaluation information by using a trained machine learning model M.

The machine learning model M may be any machine learning model as long as the machine learning model is capable of estimating the similar evaluation information described in the present specification. For example, the machine learning model M is a machine learning model including a neural network, deep learning, and the like, but is not limited thereto. The machine learning model M may be constructed in a storage area of the information processing device 1 or may be constructed in a storage area of a server communicably connected to the information processing device 1. As an example, a case will be described below in which the machine learning model M is constructed in the storage area of the information processing device 1.

Figure 2:
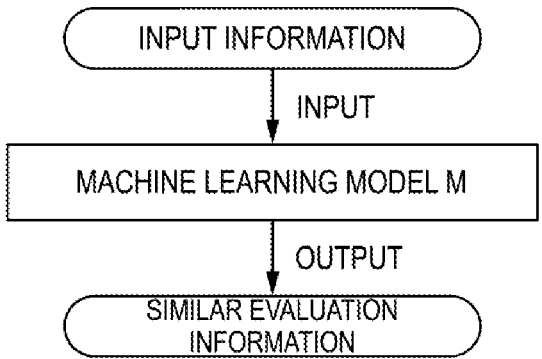
FIG. 2 is a diagram illustrating an example of input and output of a machine learning model M.

The machine learning model M has been trained such that, when the input information including the evaluation information about the user and the evaluation information about each of the plurality of model persons is input, evaluation information to which the evaluation information about the user is estimated to become close most easily among respective pieces of the evaluation information of the plurality of model persons is output as the similar evaluation information. Thus, as illustrated in FIG. 2, the machine learning model M outputs the similar evaluation information in this case. FIG. 2 is a diagram illustrating an example of input and output of the machine learning model M.

Through the processing described above, the information processing device 1 inputs the input information to the machine learning model M and generates output information including the model person information indicating the model person, among the plurality of model persons, corresponding to the similar evaluation information output from the machine learning model M. The information processing device 1 outputs the generated output information. Accordingly, the information processing device 1 can accurately output the model person information indicating the model person appropriate as a goal of the user.

The information processing device 1 includes, for example, a control unit 11, a storage unit 12, an input receiving unit 13, a communication unit 14, and a display unit 15. These constituent units are communicatively connected to each other via a bus (not illustrated). The information processing device 1 also communicates with another device via the communication unit 14. Further, the information processing device 1 may include another functional unit in addition to the control unit 11, the storage unit 12, the input receiving unit 13, the communication unit 14, and the display unit 15.

The control unit 11 controls the entire information processing device 1. The control unit 11 includes a processor such as a central processing unit (CPU). Further, the control unit 11 may include another processor such as a field programmable gate array (FPGA), instead of the CPU. The control unit 11 also includes a plurality of functional units implemented by the processor executing various programs stored in the storage unit 12. The control unit 11 includes, for example, a processing unit 111, an estimation unit 112, and a display control unit 113 as the plurality of functional units. Further, the control unit 11 may include another functional unit, in addition to the processing unit 111, the estimation unit 112, and the display control unit 113, by the processor executing various programs stored in the storage unit 12. In addition, some or all of the processing unit 111, the estimation unit 112, and the display control unit 113 included in the control unit 11 may be hardware functional units implemented by large scale integration (LSI), an application specific integrated circuit (ASIC), and the like.

The processing unit 111 performs various processing operations according to received operations.

The estimation unit 112 estimates the similar evaluation information using the machine learning model M.

The display control unit 113 generates various images according to the received operations. In addition, the display control unit 113 displays the generated images on the display unit 15.

The storage unit 12 is a storage device including, for example, a hard disk drive (HDD), a solid state drive (SSD), an electrically erasable programmable read only memory (EEPROM), a read only memory (ROM), and a random access memory (RAM). Further, the storage unit 12 may be an external storage device coupled by, for example, a digital input/output port such as a universal serial bus (USB) instead of those built into the information processing device 1. The storage unit 12 stores various types of information, various images, and various programs to be processed by the information processing device 1.

The input receiving unit 13 is, for example, an input device such as a keyboard, a mouse or a touch pad. Further, the input receiving unit 13 may be configured as a touch panel together with the display unit 15.

The communication unit 14 is a communication device including, for example, a digital input/output port such as a USB or an Ethernet (trade name) port.

The display unit 15 is a display device including, for example, a liquid crystal display panel or an organic electroluminescence (EL) display panel as a display included in the information processing device 1.

Details of Evaluation Information

Next, details of the evaluation information will be described.

Specifically, the evaluation information is information including waveform data indicating how to use the human body for an action to be analyzed in the first exercise. In the following description, this action will be referred to as a target action for convenience of description. When the first exercise is baseball as in this example, examples of the target action include swing of a bat and pitching, but the target action is not limited thereto. As an example, a case will be described below in which the target action is swing of a bat.

The waveform data included in the evaluation information is, for example, data based on first information about a movement of the human body for the target action and second information about how to use a first part of the human body for the target action. Here, the first part is a part to be analyzed in the first exercise among parts of the human body. Further, the first information may be information about a movement of a tool used in the first exercise. When the first exercise is baseball as in this example, examples of the tool include a bat and a glove, but the tool is not limited thereto. In addition, when the first exercise is golf, examples of the tool include a golf club, but the tool is not limited thereto. Moreover, in this case, examples of the first part include a right wrist joint, a left wrist joint, a right elbow joint, a left elbow joint, a right shoulder joint, a left shoulder joint, a right hip joint, a left hip joint, a right knee joint, a left knee joint, and a torso joint, but the first part is not limited thereto. Further, in the present specification, the torso joint refers to an intervertebral joint.

Here, in this example, examples of the first information include period information indicating a period during which the first exercise is performed, information indicating a timing of starting a posture of swinging a bat, information indicating a timing of starting the swing of the bat, information indicating a timing of reaching the latter half of the swing of the bat, information indicating a timing of contacting a ball with the bat, and information indicating a timing of completing hitting of the ball with the bat. For example, the first information can be detected by a sensor capable of detecting a movement of an object, such as a motion capture. Further, the first information may be information including other information about a movement of the human body for the target action instead of some or all of these pieces of information or in addition to all of these pieces of information.

On the other hand, in this example, the second information is represented by, for example, a value indicating how to use the first part in the period indicated by the period information of the first information. This value is, for example, an output value from a myoelectric sensor attached to the first part. In this case, the value representing the second information is detected by the myoelectric sensor. Further, the value representing the second information may be another value indicating how to use the first part during the period.

Figure 3:
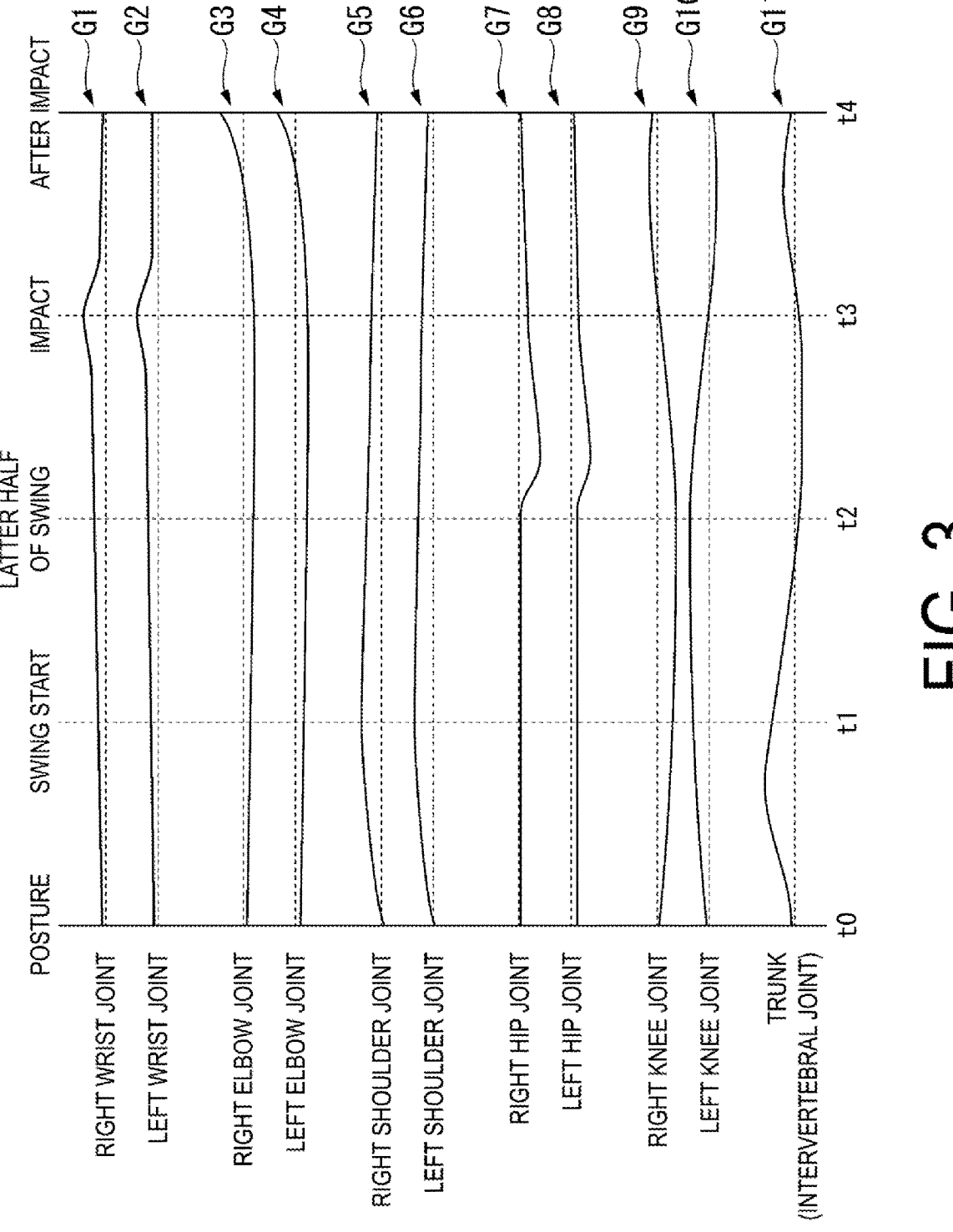
FIG. 3 is a diagram illustrating graphs in which waveforms indicated by waveform data generated based on first information and second information are plotted.

The waveform data included in the evaluation information is generated based on such first information and second information. Here, FIG. 3 is a diagram illustrating graphs in which waveforms indicated by the waveform data generated based on the first information and the second information are plotted. FIG. 3 illustrates 11 graphs G1 to G11. The horizontal axis of these 11 graphs represents the elapsed time in the period indicated by the period information of the first information. In FIG. 3, the horizontal axis is shared between the graph G1 and the graph G11. A timing t0 illustrated in FIG. 3 is an example of a timing of starting a posture of swinging a bat. In FIG. 3, the timing t0 is indicated by "posture". A timing t1 illustrated in FIG. 3 is an example of a timing of starting the swing of the bat. In FIG. 3, the timing t1 is indicated by "swing start". A timing t2 illustrated in FIG. 3 is an example of a timing of reaching the latter half of the swing of the bat. In FIG. 3, the timing t2 is indicated by "latter half of swing". A timing t3 illustrated in FIG. 3 is an example of a timing of contacting a ball with the bat. In FIG. 3, the timing t3 is indicated by "impact". A timing t4 illustrated in FIG. 3 is an example of a timing of completing hitting of the ball with the bat. In FIG. 3, the timing t4 is indicated by "after impact". In this manner, in the example illustrated in FIG. 3, the horizontal axis of the 11 graphs are generated based on the first information.

On the other hand, each vertical axis of the 11 graphs indicates the output value from the myoelectric sensor attached to the first part. That is, each of the 11 graphs is a graph indicating an example of how to use the first part in the period indicated by the period information of the first information. The graph G1 is a graph obtained by plotting the waveform indicated by the waveform data when the first part is the right wrist joint. Thus, the curve plotted in the graph G1 shows an example of the waveform indicated by the waveform data in this case. The graph G2 is a graph obtained by plotting the waveform indicated by the waveform data when the first part is the left wrist joint. Thus, the curve plotted in the graph G2 shows an example of the waveform indicated by the waveform data in this case. The graph G3 is a graph obtained by plotting the waveform indicated by the waveform data when the first part is the right elbow joint. Thus, the curve plotted in the graph G3 shows an example of the waveform indicated by the waveform data in this case. The graph G4 is a graph obtained by plotting the waveform indicated by the waveform data when the first part is the left elbow joint. Thus, the curve plotted in the graph G4 shows an example of the waveform indicated by the waveform data in this case. The graph G5 is a graph obtained by plotting the waveform indicated by the waveform data when the first part is the right shoulder joint. Thus, the curve plotted in the graph G5 shows an example of the waveform indicated by the waveform data in this case. The graph G6 is a graph obtained by plotting the waveform indicated by the waveform data when the first part is the left shoulder joint. Thus, the curve plotted in the graph G6 shows an example of the waveform indicated by the waveform data in this case. The graph G7 is a graph obtained by plotting the waveform indicated by the waveform data when the first part is the right hip joint. Thus, the curve plotted in the graph G7 shows an example of the waveform indicated by the waveform data in this case. The graph G8 is a graph obtained by plotting the waveform indicated by the waveform data when the first part is the left hip joint. Thus, the curve plotted in the graph G8 shows an example of the waveform indicated by the waveform data in this case. The graph G9 is a graph obtained by plotting the waveform indicated by the waveform data when the first part is the right knee joint. Thus, the curve plotted in the graph G9 shows an example of the waveform indicated by the waveform data in this case. The graph G10 is a graph obtained by plotting the waveform indicated by the waveform data when the first part is the left knee joint. Thus, the curve plotted in the graph G10 shows an example of the waveform indicated by the waveform data in this case. The graph G11 is a graph obtained by plotting the waveform indicated by the waveform data when the first part is the torso joint. Thus, the curve plotted in the graph G11 shows an example of the waveform indicated by the waveform data in this case.

Figure 4:
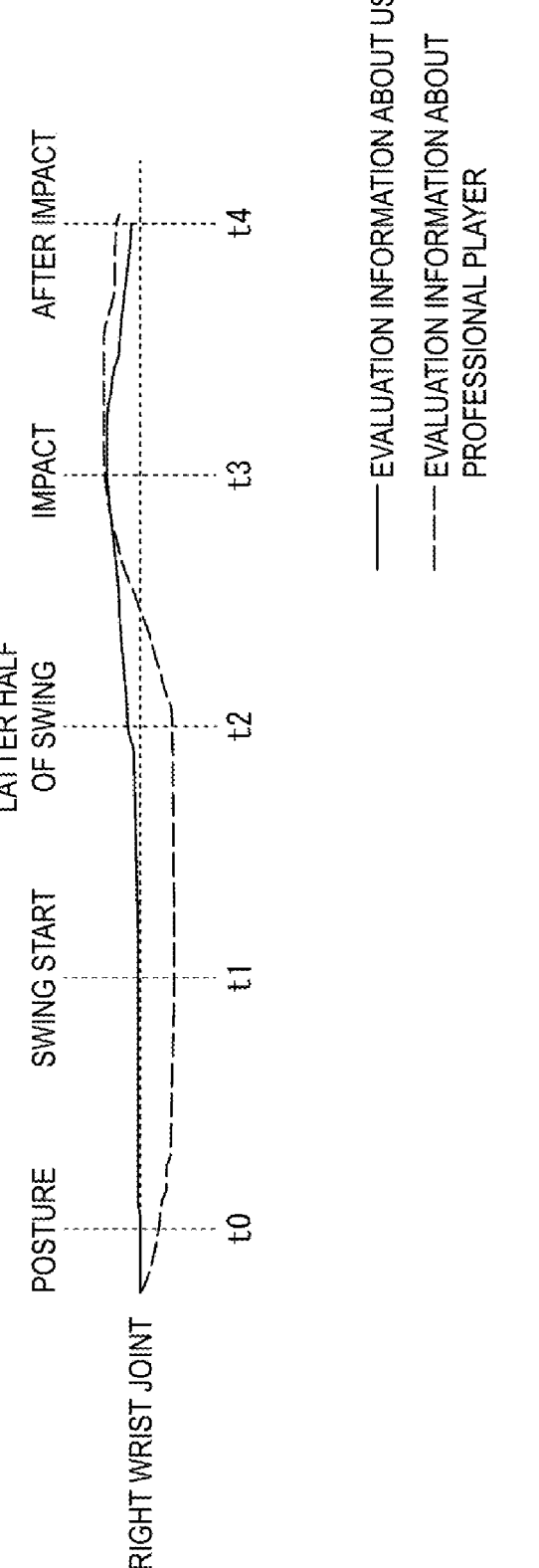
FIG. 4 is a diagram illustrating another example of a graph G1 illustrated in FIG. 3.

The evaluation information in this example includes the waveform data indicating the waveform plotted on one of the graphs G1 to G11 illustrated in FIG. 3. For example, it can be estimated that the evaluation of how the user uses the first part in the swing of the bat is higher as the waveform data included in the evaluation information about the user is closer to the waveform data included in the evaluation information about a professional player. On the other hand, for example, it can be estimated that the evaluation of how the user uses the first part in the swing of the bat is lower as the waveform data included in the evaluation information about the user is further from the waveform data included in the evaluation information about the professional player. Thus, the evaluation information indicates evaluation about the first exercise as described above. Here, FIG. 4 is a diagram illustrating another example of the graph G1 illustrated in FIG. 3. Thus, the vertical axis of the graph illustrated in FIG. 4 indicates the output value from the myoelectric sensor attached to the first part. Moreover, the horizontal axis of this graph is common to the horizontal axis of the 11 graphs illustrated in FIG. 3. As in the graph G1 illustrated in FIG. 3, in this graph, the waveform indicated by the waveform data when the first part is the right wrist joint is plotted. The waveform of the solid line in the graph is an example of the waveform indicated by the waveform data included in the evaluation information about the user. Moreover, the waveform of the dotted line in the graph is an example of the waveform indicated by the waveform data included in the evaluation information about a certain professional baseball player. The first exercise of the user is evaluated based on, for example, whether the difference between the waveform data included in the evaluation information about the user and the waveform data included in the evaluation information about the professional player at a predetermined timing is equal to or less than a predetermined threshold value. For example, it can be estimated that the evaluation of how the user uses the first part in the swing of the bat is higher as the difference between the waveform data included in the evaluation information about the user and the waveform data included in the evaluation information about the professional player is smaller than the predetermined threshold value. Specifically, in the example illustrated in FIG. 4, at the timing t3 of the impact and the timing t4 after the impact, the difference between the waveform data included in the evaluation information about the user and the waveform data included in the evaluation information about the professional player is equal to or less than the predetermined threshold value. In this case, it can be estimated that the evaluation of the swing of the bat by the user at the impact timing t3 and the timing t4 after the impact is high. On the other hand, for example, it can be estimated that the evaluation of how the user uses the first part in the swing of the bat is lower as the difference between the waveform data included in the evaluation information about the user and the waveform data included in the evaluation information about the professional player is larger than the predetermined threshold value. Specifically, in the example illustrated in FIG. 4, at the timing t0 of the posture, the timing t1 of the swing start, and the timing t2 of the latter half of the swing, the difference between the waveform data included in the evaluation information about the user and the waveform data included in the evaluation information about the professional player is larger than the predetermined threshold value. In this case, it can be estimated that the evaluation of the swing of the bat by the user at the timing t0 of the posture, the timing t1 of the swing start, and the timing t2 of the latter half of the swing is low. In this manner, the evaluation information indicates the evaluation about the first exercise as described above.

Processing of Outputting Output Information by Information Processing Device

Figure 5:
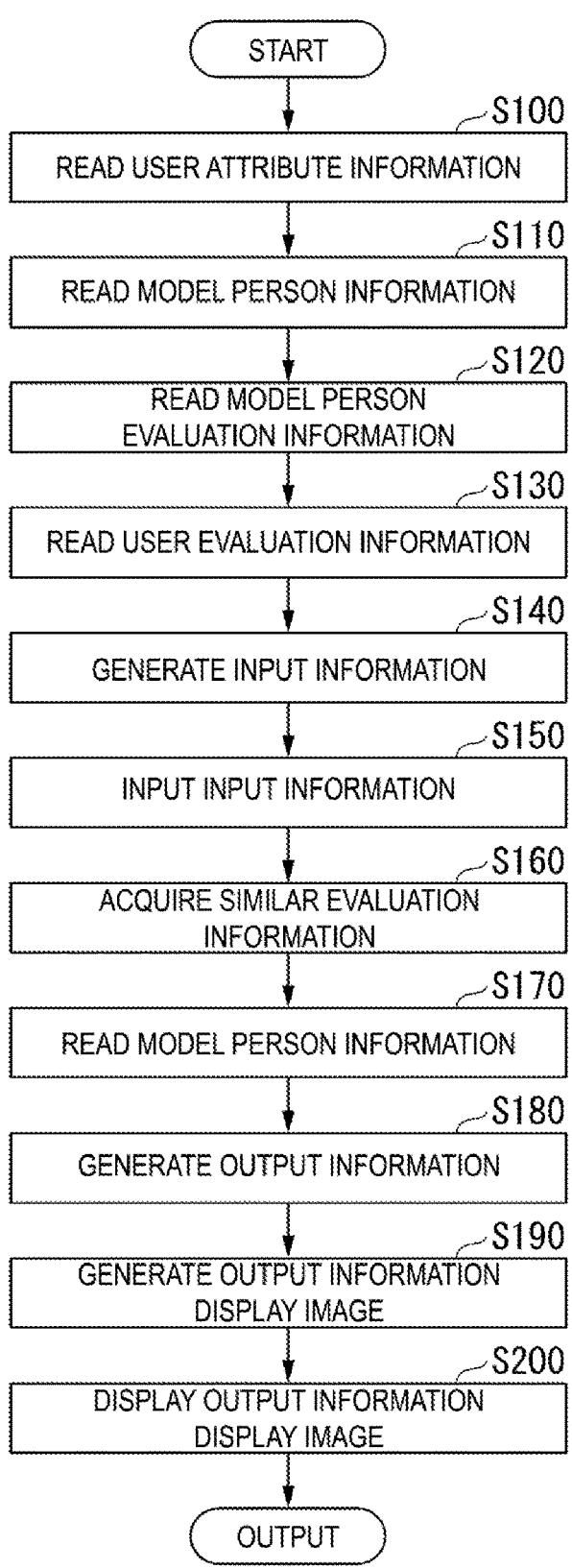
FIG. 5 is a diagram illustrating an example of a flowchart of processing of outputting output information by the information processing device 1.

Processing of outputting output information by the information processing device 1 will be described below with reference to FIG. 5. FIG. 5 is a diagram illustrating an example of a flowchart of the processing of outputting the output information by the information processing device 1. As an example, a case will be described below in which user attribute information is received by the information processing device 1 and stored in the storage unit 12 at a timing before processing of step S100 illustrated in FIG. 5. As an example, a case will be also described below in which model person information indicating each of a plurality of model persons is stored in the storage unit 12 at this timing. As an example, a case will be also described below in which evaluation information about the user is stored in the storage unit 12 at this timing. As an example, a case will be also described below in which evaluation information about each of the plurality of model persons is stored in the storage unit 12 at this timing. As an example, a case will be also described below in which the information processing device 1 receives an output processing start operation of causing the information processing device 1 to start processing of outputting the output information at this timing.

After receiving the output processing start operation, the processing unit 111 reads, from the storage unit 12, the user attribute information stored in advance in the storage unit 12 (step S100).

Next, based on the user attribute information read in step S110, the processing unit 111 identifies one or more pieces of model person information including model person attribute information indicating an attribute matching the attribute indicated by the received user attribute information from among the plurality of pieces of model person information stored in advance in the storage unit 12. Then, the processing unit 111 reads the identified one or more pieces of model person information from the storage unit 12 (step S110).

Next, the processing unit 111 reads the evaluation information about the model person indicated by each of the one or more pieces of model person information identified in step 3120 from the storage unit 12 (step S120). Since the method of identifying the evaluation information about the model person indicated by each of the one or more pieces of model person information in step S120 has already been described, a detailed description thereof will be omitted. Moreover, in the following description, the individual evaluation information identified by the processing unit 111 in step S120 will be referred to as model person evaluation information as illustrated in FIG. 5 for convenience of description.

Next, the processing unit 111 reads, from the storage unit 12, the evaluation information about the user stored in advance in the storage unit 12 (step S130). In the following description, the evaluation information about the user will be referred to as user evaluation information as illustrated in FIG. 5 for convenience of description. Further, the processing of step S130 may be performed in parallel with at least part of the processing of step S110 to step S120, or the processing of step S130 and the processing of step S110 to step S120 may be performed in reverse order.

Next, the processing unit 111 generates information including the user evaluation information read in step S130 and the one or more pieces of model person evaluation information read in step S120 as input information (step S140).

Next, the estimation unit 112 inputs the input information generated in step S140 to the machine learning model M configured in the storage area of the storage unit 12 (step S150). As a result, the machine learning model M outputs similar evaluation information corresponding to the input information that has been input. Here, the machine learning model M is a machine learning model that has been trained such that when the input information is input, evaluation information most likely to be evaluation information to which the evaluation information about the user included in the input information that has been input becomes close easily is identified as the similar evaluation information from among the evaluation information about the plurality of model persons based on evaluation change information indicating a change in the evaluation information caused by a practice of each of a plurality of practice menus for the first exercise. A method of achieving such training may be a known method or a method to be developed in the future. In addition, since such training is performed, when the input information is input, the machine learning model M identifies, as the similar evaluation information, model person evaluation information most likely to be evaluation information to which the evaluation information about the user included in the input information that has been input becomes close easily from among the one or more pieces of model person evaluation information read in step S120. In this process, the machine learning model M calculates, for each piece of the waveform data of the one or more pieces of model person evaluation information read in step S120, a likelihood indicating how likely the waveform data about the user included in the input information that has been input becomes close easily and sorts, based on the calculated likelihood, the one or more pieces of model person evaluation information in the order of the evaluation information including the waveform data having the high likelihood. Then, the machine learning model M identifies, as the similar evaluation information, the model person evaluation information including the waveform data having the highest likelihood from among the one or more pieces of model person evaluation information sorted in the order of the evaluation information including the waveform data having the high likelihood. Further, the machine learning model M may be configured to identify, as the similar evaluation information, the model person evaluation information including the waveform data corresponding to the likelihood other than the highest likelihood from among the one or more pieces of model person evaluation information sorted in the order of the evaluation information including the waveform data having the high likelihood.

Next, as a result of inputting the input information to the machine learning model M in step S150, the estimation unit 112 acquires the similar evaluation information output from the machine learning model M (step S160).

Next, the processing unit 111 reads the model person information indicating the model person corresponding to the similar evaluation information acquired in step S160 from the storage unit 12 (step S170).

Next, the processing unit 111 generates output information including the model person information acquired in step S170 (step S180).

Next, the display control unit 113 generates an image including the output information generated in step S180 as an output information display image (step S190). When the output information is information involving output of sound, the information processing device 1 includes, for example, a speaker.

Next, the display control unit 113 displays the output information display image generated in step S190 on the display unit 15 (step S200) and the processing of the flowchart illustrated in FIG. 5 ends.

As described above, the information processing device 1 uses the information indicating the evaluation about the first exercise as the evaluation information and when the input information including the user evaluation information and the one or more pieces of model person evaluation information is input, the information processing device 1 inputs the input information to the trained machine learning model M outputting, as the similar evaluation information, the model person evaluation information to which the user evaluation information is estimated to become close most easily among the one or more pieces of model person evaluation information, and outputs the output information including the model person information indicating the model person corresponding to the similar evaluation information output from the machine learning model M among the plurality of model persons. Accordingly, the information processing device 1 can accurately output the model person information indicating the model person appropriate as a goal of the user. Here, in this example, the model person information includes physical type information indicating a physical type of the model person. Thus, the information processing device 1 in this example can accurately output the model person information indicating the model person appropriate as the goal of the user and also provide the user with the physical type that the user should aspire to have. Further, the model person information may not include the physical type information.

In addition, to output the similar evaluation information as described above, when the input information is input and the evaluation information about a second user different from the first user is included in the input information, the machine learning model M outputs similar evaluation information indicating evaluation different from the evaluation indicated by the similar evaluation information output when the evaluation information about the first user is included in the input information except for the case of coincidence. Thus, the information processing device 1 can accurately output the model person information indicating the model person appropriate as a goal of each user.

Modified Example 1 of Embodiment

Modified Example 1 of the embodiment will be described below. In the example described above, the evaluation information includes one type of waveform data. However, the evaluation information may include two or more types of waveform data. For example, the waveform data included in the evaluation information may be two types of waveform data of first waveform data and second waveform data. The first waveform data is waveform data based on the first information about a movement of the human body for a target action and the second information about how to use the first part in the target action. Moreover, the second waveform data is waveform data based on the first information and third information about how to use a second part of the human body in the target action. Here, the second part may be any part of the human body as long as the second part is different from the first part. As an example, a case will be described below in which the first part is the right wrist joint and the second part is the torso joint. In this case, the first waveform data is waveform data indicating how to use the right wrist joint for the target action. Moreover, in this case, the second waveform data is waveform data indicating how to use the torso joint for the target action.

In a case where the two types of waveform data are included in the evaluation information as described above, when input information is input, the machine learning model M identifies, as similar evaluation information, evaluation information most likely to include first waveform data to which the first waveform data about the user included in the input information that has been input becomes close easily and second waveform data to which the second waveform data about the user included in the input information that has been input becomes close easily from among the respective pieces of the evaluation information about the plurality of model persons. In this process, the machine learning model M calculates, for each piece of the evaluation information about the plurality of model persons, a likelihood indicating how likely the evaluation information includes first waveform data to which the first waveform data about the user included in the input information that has been input becomes close easily and second waveform data to which the second waveform data about the user included in the input information that has been input becomes close easily, and sorts, based on the calculated likelihood, the evaluation information about each of the plurality of model persons in descending order of the likelihood. Then, the machine learning model M outputs, as the similar evaluation information, the evaluation information corresponding to the highest likelihood among the evaluation information about each of the plurality of model persons sorted in descending order of the likelihood. In this case as well, the machine learning model M is a machine learning model that has been trained such that when the input information is input, evaluation information most likely to be evaluation information to which the evaluation information about the user included in the input information that has been input becomes close easily is identified as the similar evaluation information from among the evaluation information about the plurality of model persons based on the evaluation change information indicating a change in the evaluation information caused by the practice in each of the plurality of practice menus for the first exercise. A method of achieving such training may be a known method or a method to be developed in the future.

With the above-described configuration, even when the evaluation information includes two or more types of waveform data, the information processing device 1 can accurately output the model person information indicating the model person appropriate as a goal of the user. In addition, in this case, the information processing device 1 can more reliably and accurately output the model person information indicating the model person appropriate as a goal of the user.

Modified Example 2 of Embodiment

Figure 6:
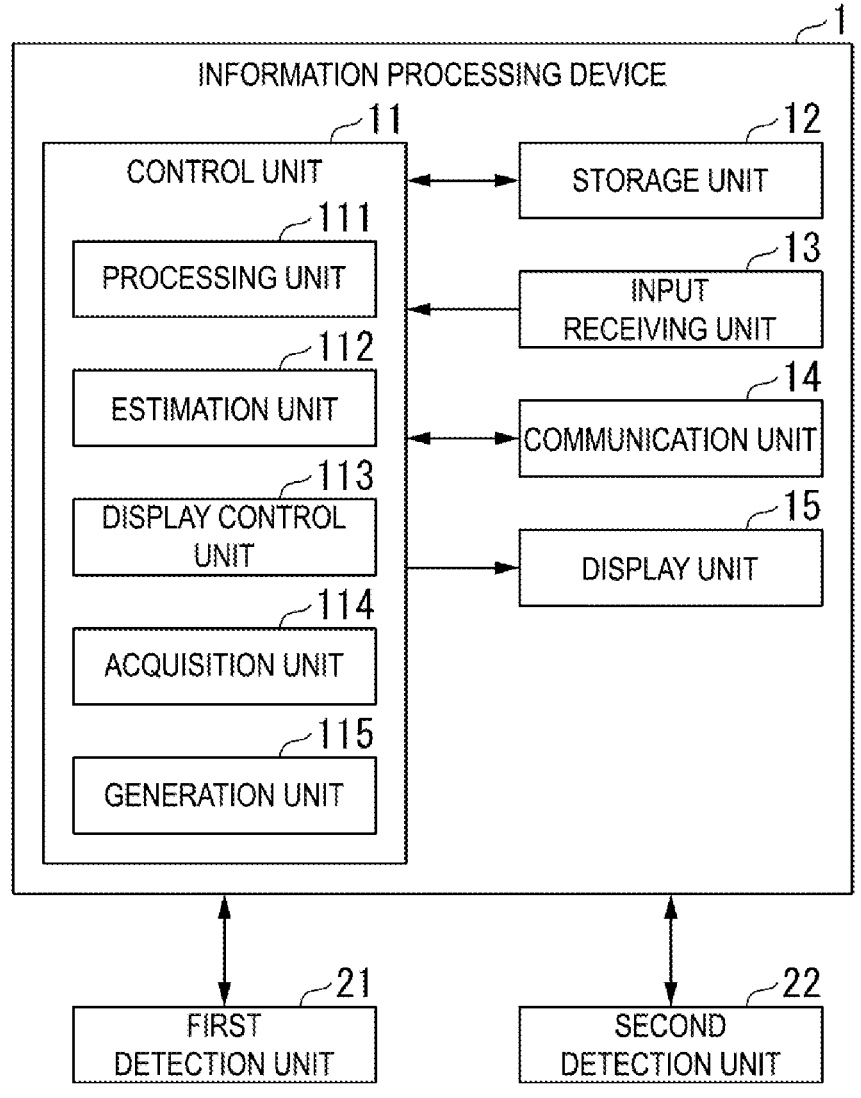
FIG. 6 is a diagram illustrating another example of the configuration of the information processing device 1.

Modified Example 2 of the embodiment will be described below. In Modified Example 2 of the embodiment, the information processing device 1 generates evaluation information. Thus, in the Modified Example 2 of the embodiment, as illustrated in FIG. 6, the information processing device 1 is communicably connected to each of a first detection unit 21 and a second detection unit 22 in a wireless or wired manner. FIG. 6 is a diagram illustrating another example of the configuration of the information processing device 1. Further, the information processing device 1 may include the first detection unit 21 and the second detection unit 22 or may not include the first detection unit 21 or the second detection unit 22.

The first detection unit 21 is a sensor detecting the first information and is, for example, a motion capture. Further, the first detection unit 21 may be another sensor capable of detecting the first information instead of the motion capture.

The second detection unit 22 is a sensor detecting a value representing the second information and is, for example, a myoelectric sensor. Further, the second detection unit 22 may be another sensor capable of detecting the value representing the second information instead of the myoelectric sensor.

When the information processing device 1 is communicably connected to each of the first detection unit 21 and the second detection unit 22 in this manner, the control unit 11 of the information processing device 1 includes an acquisition unit 114 and a generation unit 115 in addition to the processing unit 111, the estimation unit 112, and the display control unit 113.

The acquisition unit 114 acquires, from the first detection unit 21, the first information detected by the first detection unit 21. Moreover, the acquisition unit 114 acquires, from the second detection unit 22, the value representing the second information detected by the second detection unit 22.

The generation unit 115 generates evaluation information based on the first information acquired by the acquisition unit 114 and the value representing the second information acquired by the acquisition unit 114.

Figure 7:
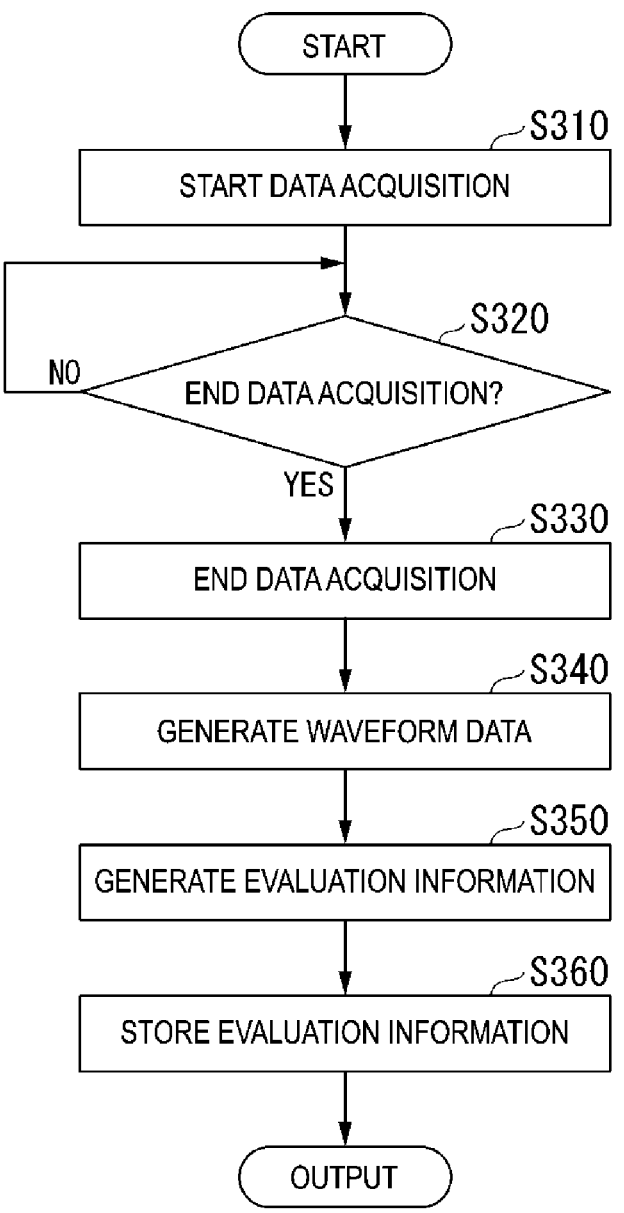
FIG. 7 is a diagram illustrating an example of a flowchart of processing of generating evaluation information by the information processing device 1.

Next, processing of generating the evaluation information by the information processing device 1 will be described below with reference to FIG. 7. FIG. 7 is a diagram illustrating an example of a flowchart of the processing of generating the evaluation information by the information processing device 1. As an example, a case will be described below in which the information processing device 1 receives an operation of causing the information processing device 1 to start the processing of generating the evaluation information at a timing before the processing of step S310 illustrated in FIG. 7. As an example, a case will be also described below in which the user is located at a position where the first information can be detected by the first detection unit 21 and the second detection unit 22 is attached to the first part of the user at this timing. In this case, the evaluation information generated by the information processing device 1 is evaluation information about the user. When the information processing device 1 generates the evaluation information about a person other than the user, such as a first model person, this person is located at a position where the first information can be detected by the first detection unit 21. In this case, the second detection unit 22 is also attached to the first part of this person. As an example, a case will be also described below in which preparation for the user to perform a target action has been completed at this timing.

After receiving the operation of causing the information processing device 1 to start the processing of generating the evaluation information, the acquisition unit 114 starts acquiring the first information from the first detection unit 21 and acquiring the value representing the second information from the second detection unit 22 (step S310). Then, the display control unit 113 generates an image including information for prompting the user to start the target action and displays the generated image on the display unit 15. Thus, the user can start the target action. Further, the information processing device 1 may be configured to output sound indicating the information. In this case, the information processing device 1 includes a speaker. In FIG. 7, the processing of step 3130 is indicated by "data acquisition start".

Next, the acquisition unit 114 determines whether to end the acquisition of the first information from the first detection unit 21 and the acquisition of the value representing the second information from the second detection unit 22 (step S320). In FIG. 7, the processing of step S320 is indicated by "end data acquisition?". For example, in step S320, the acquisition unit 114 determines whether the user has ended the target action based on the first information acquired from the first detection unit 21. Here, a method of determining whether the user has ended the target action based on the first information acquired from the first detection unit 21, which is a motion capture, may be a known method or a method to be developed in the future. When determining that the user has ended the target action, the acquisition unit 114 determines to end the acquisition of the first information from the first detection unit 21 and the acquisition of the value representing the second information from the second detection unit 22. On the other hand, when determining that the user has not ended the target action, the acquisition unit 114 determines not to end the acquisition of the first information from the first detection unit 21 and the acquisition of the value representing the second information from the second detection unit 22. Further, the method of determining whether the user has ended the target action may be another method instead of the method based on the first information. In addition, in step S320, the acquisition unit 114 may be configured to determine whether to end the acquisition of the first information from the first detection unit 21 and the acquisition of the value representing the second information from the second detection unit 22 by another method.

When determining not to end the acquisition of the first information from the first detection unit 21 and the acquisition of the value representing the second information from the second detection unit 22 (NO in step S320), the acquisition unit 114 continues to acquire the first information from the first detection unit 21 and the value representing the second information from the second detection unit 22.

On the other hand, when determining to end the acquisition of the first information from the first detection unit 21 and the acquisition of the value representing the second information from the second detection unit 22 (YES in Step S320), the acquisition unit 114 ends the acquisition of the first information from the first detection unit 21 and the acquisition of the value representing the second information from the second detection unit 22 (Step S330). In FIG. 7, the processing of step S330 is indicated by "data acquisition end".

Next, the generation unit 115 generates waveform data based on the first information and the second information acquired by the processing in steps S310 to S330 (step S340).

Next, the generation unit 115 generates evaluation information including the waveform data generated in step S340 (step S350).

Next, the generation unit 115 stores the evaluation information generated in step S350 in the storage unit 12 (step S360) and the processing of the flowchart illustrated in FIG. 7 ends.

As described above, the information processing device 1 can generate the evaluation information. Further, examples of the evaluation information about a certain person include identification information for identifying the person and date and time information indicating the date and time at which the evaluation information is generated. Thus, the information processing device 1 can identify whose evaluation information is evaluation information stored in the storage unit 12.

Modified Example 3 of Embodiment

Modified Example 3 of the embodiment will be described below. In Modified Example 3 of the embodiment, certain evaluation change information is information indicating a change in evaluation information caused by a practice of a certain practice menu for the first exercise and is information associated with practice menu information indicating the practice menu. In this case, the machine learning model M is a machine learning model that has been trained such that when input information is input, evaluation information most likely to be evaluation information to which the evaluation information about the user included in the input information that has been input becomes close easily is identified as similar evaluation information from among the evaluation information about the plurality of model persons based on the evaluation change information associated with the practice menu information. In this case, the machine learning model M outputs practice menu information associated with the similar evaluation information as practice menu information indicating a practice menu appropriate for the user among the plurality of practice menus, together with the similar evaluation information identified as described above. Thus, the information processing device 1 outputs output information including the practice menu information associated with the similar evaluation information together with the similar evaluation information. As a result, the information processing device 1 can accurately output the model person information indicating the model person appropriate as a goal of the user and also provide the user with the practice menu of the practice necessary for the user to become close to the model person.

Modified Example 4 of Embodiment

Modified Example 4 of the embodiment will be described below. In Modified Example 4 of the embodiment, the information processing device 1 provides the user with an exercise appropriate for the user among a plurality of exercises instead of providing the user with a model person appropriate as a goal of the user among the plurality of model persons. In this case, the storage unit 12 of the information processing device 1 stores a plurality of pieces of model person information for each of N types of exercises from a first exercise to an N-th exercise. In this case, each piece of the model person information stored in the storage unit 12 includes exercise information indicating an exercise in which the model person indicated by the model person information shows a good performance as a player. Moreover, in this case, the storage unit 12 of the information processing device 1 stores evaluation information about the model person for each of the N types of exercises. When receiving user attribute information, the information processing device 1 identifies one or more pieces of model person information including attribute information indicating an attribute matching the attribute indicated by the received user attribute information from among the plurality of pieces of model person information stored in the storage unit 12. Then, the information processing device 1 inputs, to the machine learning model M, input information including the evaluation information about the model person indicated by each of the identified one or more pieces of model person information and the evaluation information about the user. As a result, the machine learning model M outputs similar evaluation information through the processing described in the embodiment. The information processing device 1 reads, from the storage unit 12, model person information indicating a model person corresponding to the similar evaluation information output from the machine learning model M and displays exercise information included in the read model person information on the display unit 15 as exercise information indicating an exercise appropriate for the user. In this way, the information processing device 1 can provide the user with the exercise appropriate for the user.

Modified Example 5 of Embodiment

Modified Example 5 of the embodiment will be described below. In Modified Example 5 of the embodiment, the information processing device 1 may be configured to receive user attribute information and then display physical type information indicating a physical type appropriate for the user based on the received user attribute information and evaluation information about the user stored in advance in the storage unit 12. In this case, the information processing device 1 identifies one or more pieces of model person information including model person attribute information indicating an attribute matching the attribute indicated by the received user attribute information from among the model person information stored in advance. The information processing device 1 identifies evaluation information including waveform data closest to the waveform data of the evaluation information about the user from among the evaluation information about the model person indicated by each of the identified one or more pieces of model person information. Then, the information processing device 1 displays, on the display unit 15, physical type information included in the model person information indicating the model person corresponding to the identified evaluation information. Thus, the information processing device 1 can notify the user of the physical type that the user can easily aspire to have.

Details of Evaluation Change Information

Details of the evaluation change information used for training of the machine learning model M will be described below. A plurality of pieces of the evaluation change information are used for training of the machine learning model M. The plurality of pieces of evaluation change information each are evaluation change information about each of a plurality of persons. In the following description, each of the plurality of persons will be referred to as a teacher for convenience of description. The evaluation change information about a certain teacher is information indicating a change in the evaluation information about the teacher caused by a practice of each of a plurality of practice menus. More specifically, the evaluation change information about the teacher is information indicating a change in the waveform data of the evaluation information about the teacher caused by a practice of each of the plurality of practice menus. Specifically, examples of the evaluation change information about the teacher include evaluation change information about the teacher for each of the plurality of practice menus. Examples of the evaluation change information about the teacher of a certain practice menu include evaluation information about the teacher before a practice of the practice menu and evaluation information about the teacher after the practice of the practice menu. This is because the difference between the waveform data of these two pieces of evaluation information indicates a change in the evaluation information about the teacher caused by the practice of the practice menu. Further, the evaluation change information about a certain teacher may be other information indicating a change in the evaluation information about the teacher caused by the practice of each of the plurality of practice menus.

For example, when causing the machine learning model M to learn the evaluation change information about a certain teacher of a certain practice menu according to a received operation, the information processing device 1 causes the machine learning model M to learn the evaluation change information using the waveform data of each of the two pieces of evaluation information included in the evaluation change information as teacher data and using the similarity between the two pieces of evaluation information as a correct label. Then, according to the received operation, the information processing device 1 causes the machine learning model M to learn such evaluation change information for each combination of the plurality of practice menus and the plurality of teachers. Accordingly, when input information is input, the information processing device 1 can train the machine learning model M so as to identify, as similar evaluation information, evaluation information most likely to be evaluation information to which the evaluation information about the user included in the input information that has been input becomes close easily from among the evaluation information about the plurality of model persons. Further, the similarity between these two pieces of evaluation information may be calculated by a known method or may be calculated by a method to be developed in the future. Moreover, the similarity between these two pieces of evaluation information may be calculated by the information processing device 1, may be calculated by another device, may be calculated by the user, or may be calculated by another method. Furthermore, the evaluation information about the teacher is generated by, for example, the processing of the flowchart illustrated in FIG. 7. The evaluation change information may be also generated by the information processing device 1 or may be generated by another device.

Further, those described above may be combined in any manner.

As described above, the information processing device according to the embodiment includes the control unit configured to use information indicating the evaluation about the first exercise as the evaluation information, input the input information including the evaluation information about the first person and respective pieces of the evaluation information about the plurality of model persons to the machine learning model trained, and output the output information including the model person information indicating the model person, among the plurality of model persons, corresponding to the similar evaluation information output from the machine learning model, the machine learning model being configured to, when the input information is input, output, as the similar evaluation information, a piece of the evaluation information that, among respective pieces of the evaluation information of the plurality of model persons, is estimated to be most easily approachable by the evaluation information about the first person. Accordingly, the information processing device can accurately output the model person information indicating the model person appropriate as a goal of the user.

Supplementary Description

[1]

An information processing device including a control unit configured to use information indicating evaluation about a first exercise as evaluation information, input input information including the evaluation information about a first person and respective pieces of the evaluation information about a plurality of model persons to a machine learning model trained, and output output information including model person information indicating a model person, among the plurality of model persons, corresponding to similar evaluation information output from the machine learning model, the machine learning model being configured to, when the input information is input, output, as the similar evaluation information, a piece of the evaluation information that, among respective pieces of the evaluation information of the plurality of model persons, is estimated to be most easily approachable by the evaluation information about the first person.

[2]

The information processing device according to [1], wherein when the input information is input, the machine learning model outputs practice menu information indicating a practice menu appropriate for the first person among a plurality of practice menus for the first exercise, together with the model person information.

[3]

The information processing device according to [1] or [2], wherein information indicating an attribute is used as attribute information, and each of the plurality of model persons is associated with the attribute information about the model person, and the control unit identifies one or more model persons associated with the attribute information matching the attribute information about the first person from among the plurality of model persons in accordance with a received operation, and generates the input information including the evaluation information about each of the one or more model persons identified and the evaluation information about the first person.

[4]

The information processing device according to [3], wherein the attribute information includes at least one of age group information indicating an age group or physique information indicating a physique.

[5]

The information processing device according to any one of [1] to [4], wherein the machine learning model is trained such that when the input information is input, the evaluation information most likely to be the evaluation information to which the evaluation information about the first person included in the input information that is input becomes close easily is identified as the similar evaluation information from among the respective pieces of the evaluation information about the plurality of model persons based on evaluation change information indicating a change in the evaluation information caused by respective practices of a plurality of practice menus for the first exercise.

[6]

The information processing device according to [5], wherein the evaluation information includes waveform data indicating how to use a human body for an action to be analyzed in the first exercise, the evaluation change information indicates a change caused in the waveform data, and when the input information is input, the machine learning model identifies, from among respective pieces of the waveform data of the plurality of model persons, the waveform data to which the waveform data about the first person included in the input information that is input is most likely to become close easily, and identifies, as the similar evaluation information, the evaluation information including the waveform data identified.

[7]

The information processing device according to [6], wherein the waveform data is data based on first information about a movement of an object for the action and second information about how to use a first part of the human body in the action, and the object is the human body or a tool used in the first exercise.

[8]

The information processing device according to [6], wherein the waveform data includes first waveform data based on first information about a movement of an object for the action and second information about how to use a first part of the human body in the action, and second waveform data based on the first information and third information about how to use a second part of the human body in the action, and the object is the human body or a tool used in the first exercise.

[9]

The information processing device according to any one of [1] to [8], wherein when the input information is input and the evaluation information about a second person different from the first person is included in the input information, the machine learning model outputs the similar evaluation information indicating evaluation different from evaluation indicated by the similar evaluation information output when the evaluation information about the first person is included in the input information.

[10]

An information processing method including, provided that information indicating evaluation about a first exercise is evaluation information, inputting input information including the evaluation information about a first person and respective pieces of the evaluation information about a plurality of model persons to a machine learning model trained, and being configured to, when the input information is input, output information including model person information indicating a model person, among the plurality of model persons, corresponding to similar evaluation information output from the machine learning model, the machine learning model being configured to, when the input information is input, output, as the similar evaluation information, a piece of the evaluation information that, among respective pieces of the evaluation information of the plurality of model persons, is estimated to be most easily approachable by the evaluation information about the first person.

[11]

A non-transitory computer-readable storage medium storing a program, the program causing a computer to execute, provided that information indicating evaluation about a first exercise is evaluation information, inputting input information including the evaluation information about a first person and respective pieces of the evaluation information about a plurality of model persons to a machine learning model trained, and outputting output information including model person information indicating a model person, among the plurality of model persons, corresponding to similar evaluation information output from the machine learning model, the machine learning model being configured to, when the input information is input, output, as the similar evaluation information, a piece of the evaluation information that, among respective pieces of the evaluation information of the plurality of model persons, is estimated to be most easily approachable by the evaluation information about the first person.

Although the embodiment of this disclosure has been described in detail with reference to the drawings, the specific configurations are not limited to this embodiment and may be, for example, modified, substituted, and deleted unless these configurations depart from the spirit of the disclosure.

In addition, a program for implementing the functions of any constituent units of the device described above may be recorded in a computer-readable recording medium, and the program may be read and executed by a computer system. Here, the device is, for example, the information processing device 1. Further, the "computer system" mentioned here is assumed to include an operating system (OS) and hardware such as a peripheral apparatus. Furthermore, the "computer-readable recording medium" refers to a portable medium such as a flexible disk, a magneto-optical disk, a ROM, a compact disc (CD)-ROM, and a storage device such as a hard disk built into a computer system. Furthermore, the "computer-readable recording medium" is assumed to include one that holds the program for a certain period of time, such as volatile memory inside the computer system serving as a server or a client when the program is transmitted via a network such as the Internet or a communication line such as a telephone line.

In addition, the program described above may be transmitted from the computer system storing the program in the storage device or the like to another computer system via a transmission medium or transmission waves in the transmission medium. Here, the "transmission medium" for transmitting the program refers to a medium having a function of transmitting information, like a network such as the Internet or a communication line such as a telephone line.

In addition, the above-described program may be to implement some of the functions described above. Furthermore, the above-described program can be a so-called differential file or a differential program that can implement the above-described functions in combination with a program already recorded in the computer system.

What is claimed is:

1. An information processing device comprising
a control unit configured to,
provided that information indicating evaluation about a first exercise is evaluation information,
input information including the evaluation information about a first person and respective pieces of the evaluation information about a plurality of model persons to a machine learning model trained, and
output information including model person information indicating a model person, among the plurality of model persons, corresponding to similar evaluation information output from the machine learning model,
the machine learning model being configured to, when the input information is input, output, as the similar evaluation information, a piece of the evaluation information that, among the respective pieces of the evaluation information about the plurality of model persons, is estimated to be most easily approachable by the evaluation information about the first person;
a motion capture sensor configured to detect movement data of a human body performing the first exercise; and
a myoelectric sensor configured to detect electrical activity data from at least one part of the human body during performance of the first exercise, wherein
the control unit is further configured to generate the evaluation information as waveform data based on the movement data from the motion capture sensor and the electrical activity data from the myoelectric sensor, and
the machine learning model is trained using evaluation change information indicating changes in evaluation information resulting from users performing different training exercises, the machine learning model being configured to output the evaluation information that is estimated to be most achievable by the first person based on the evaluation change information.

2. The information processing device according to claim 1, wherein when the input information is input, the machine learning model outputs practice menu information indicating a practice menu appropriate for the first person among a plurality of practice menus for the first exercise, together with the model person information.

3. The information processing device according to claim 1, wherein information indicating an attribute is used as attribute information, and each of the plurality of model persons is associated with the attribute information about the model person, and the control unit identifies one or more model persons associated with the attribute information matching the attribute information about the first person from among the plurality of model persons in accordance with a received operation, and generates the input information including the evaluation information about each of the one or more model persons identified and the evaluation information about the first person.

4. The information processing device according to claim 3, wherein the attribute information includes at least one of age group information indicating an age group or physique information indicating a physique.

5. The information processing device according to claim 1, wherein
the evaluation change information indicates changes in the evaluation information caused by respective practices of a plurality of practice menus for the first exercise.

6. The information processing device according to claim 5, wherein
the evaluation information includes waveform data indicating how to use a human body for an action to be analyzed in the first exercise,
the evaluation change information indicates a change caused in the waveform data, and
when the input information is input, the machine learning model identifies, from among respective pieces of the waveform data about the plurality of model persons, the waveform data most easily approachable by the waveform data about the first person included in the input information that is input, and identifies, as the similar evaluation information, the evaluation information including the waveform data identified.

7. The information processing device according to claim 6, wherein the waveform data is data based on first information about a movement of an object for the action and second information about how to use a first part of the human body in the action, and the object is the human body or a tool used in the first exercise.

8. The information processing device according to claim 6, wherein the waveform data includes first waveform data based on first information about a movement of an object for the action and second information about how to use a first part of the human body in the action, and second waveform data based on the first information and third information about how to use a second part of the human body in the action, and the object is the human body or a tool used in the first exercise.

9. The information processing device according to claim 1, wherein when the input information is input and the evaluation information about a second person different from the first person is included in the input information, the machine learning model outputs the similar evaluation information indicating evaluation different from evaluation indicated by the similar evaluation information output when the evaluation information about the first person is included in the input information.

10. An information processing method comprising:

provided that information indicating evaluation about a first exercise is evaluation information, inputting input information including the evaluation information about a first person and respective pieces of the evaluation information about a plurality of model persons to a machine learning model trained, and outputting output information including model person information indicating a model person, among the plurality of model persons, corresponding to similar evaluation information output from the machine learning model, the machine learning model being configured to, when the input information is input, output, as the similar evaluation information, a piece of the evaluation information that, among respective pieces of the evaluation information of the plurality of model persons, is estimated to be most easily approachable by the evaluation information about the first person;

detecting, by a motion capture sensor, movement data of a human body performing the first exercise;

detecting, by a myoelectric sensor, electrical activity data from at least one part of the human body during performance of the first exercise; and generating the evaluation information as waveform data based on the movement data and the electrical activity data, wherein the machine learning model is trained using evaluation change information indicating changes in evaluation information resulting from users performing different training exercises, the machine learning model being configured to output the evaluation information that is estimated to be most achievable by the first person based on the evaluation change information.

11. A non-transitory computer-readable storage medium storing a program, the program causing a computer to execute:

provided that information indicating evaluation about a first exercise is evaluation information, inputting input information including the evaluation information about a first person and respective pieces of the evaluation information about a plurality of model persons to a machine learning model trained, and outputting output information including model person information indicating a model person, among the plurality of model persons, corresponding to similar evaluation information output from the machine learning model, the machine learning model being configured to, when the input information is input, output, as the similar evaluation information, a piece of the evaluation information that, among respective pieces of the evaluation information of the plurality of model persons, is estimated to be most easily approachable by the evaluation information about the first person;

detecting, by a motion capture sensor, movement data of a human body performing the first exercise;

detecting, by a myoelectric sensor, electrical activity data from at least one part of the human body during performance of the first exercise; and generating the evaluation information as waveform data based on the movement data and the electrical activity data, wherein the machine learning model is trained using evaluation change information indicating changes in evaluation information resulting from users performing different training exercises, the machine learning model being configured to output the evaluation information that is estimated to be most achievable by the first person based on the evaluation change information.

* * * * *